US00PP21779P3

(12) United States Plant Patent
Rampp

(10) Patent No.: US PP21,779 P3
(45) Date of Patent: Mar. 15, 2011

(54) **VARIETY OF *HYDRANGEA* PLANT NAMED 'STRAMADSCHI'**

(50) Latin Name: *Hydrangea macrophylla*
Varietal Denomination: Stramadschi

(75) Inventor: Franz-Xaver Rampp, Mindelheim (DE)

(73) Assignee: Kwekerij 'De Stadsweiden', Harderwijk (NL)

( * ) Notice: Subject to any disclaimer, the term of this patent is extended or adjusted under 35 U.S.C. 154(b) by 47 days.

(21) Appl. No.: 12/384,251

(22) Filed: Apr. 2, 2009

(65) Prior Publication Data

US 2010/0257648 P1 Oct. 7, 2010

(51) Int. Cl.
*A01H 5/00* (2006.01)

(52) U.S. Cl. ..... Plt./250
(58) Field of Classification Search ..... Plt./250

See application file for complete search history.

(56) References Cited

PUBLICATIONS

GTITM UPOVROM Citation for 'Stramadschi' as per QZ PBR 20052494; Nov. 28, 2005.*

* cited by examiner

*Primary Examiner*—Kent L Bell
(74) *Attorney, Agent, or Firm*—The Webb Law Firm

(57) ABSTRACT

A new and distinct *Hydrangea* plant having red-colored flowers and black-colored, strong stems.

2 Drawing Sheets

Botanical classification: *Hydrangea macrophylla.*
Varietal denomination: 'STRAMADSCHI'.

BACKGROUND OF THE INVENTION

The present invention comprises a new and distinct cultivar of *Hydrangea* plant known by the varietal name 'Stramadschi'. The new variety was discovered in 2003 in a planned breeding program in Salgen-Hausen, Germany. The purpose of the breeding program was to develop *Hydrangeas* with improved flower colors and black stems. The new variety is the result of a cross between seedling G6 (female parent, unpatented) and 'Paris Rapa' (male parent, U.S. Plant Pat. No. 10,906). The black stem color of 'Stramadschi' is similar to its female parent, but it differs from seedling G6 in flower color. The flowers of 'Stramadschi' are similar to 'Paris Rapa', but its leaf shape, black stem and red flower color are different from 'Paris Rapa'. The new variety was first asexually reproduced in 2004 via propagation by cuttings in Salgen-Hausen, Germany. The new variety has been trial and field tested in Germany and has been found to retain its distinctive characteristics and remain true to type through successive propagations.

The following traits distinguish 'Stramadschi' as a new and distinct cultivar from other *Hydrangea* varieties known to the breeder:

1. Black stem color instead of green stem color;
2. Red flower color;
3. Frost resistance;
4. Stem strength; and
5. Mold resistance, such as botrytis.

'Stramadschi' is similar to another *Hydrangea* variety, 'Stramalyn' (U.S. Plant patent application Ser. No. 12/384,252), because they both have black stems that are strong. However, 'Stramadschi' differs from 'Stramalyn' in flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
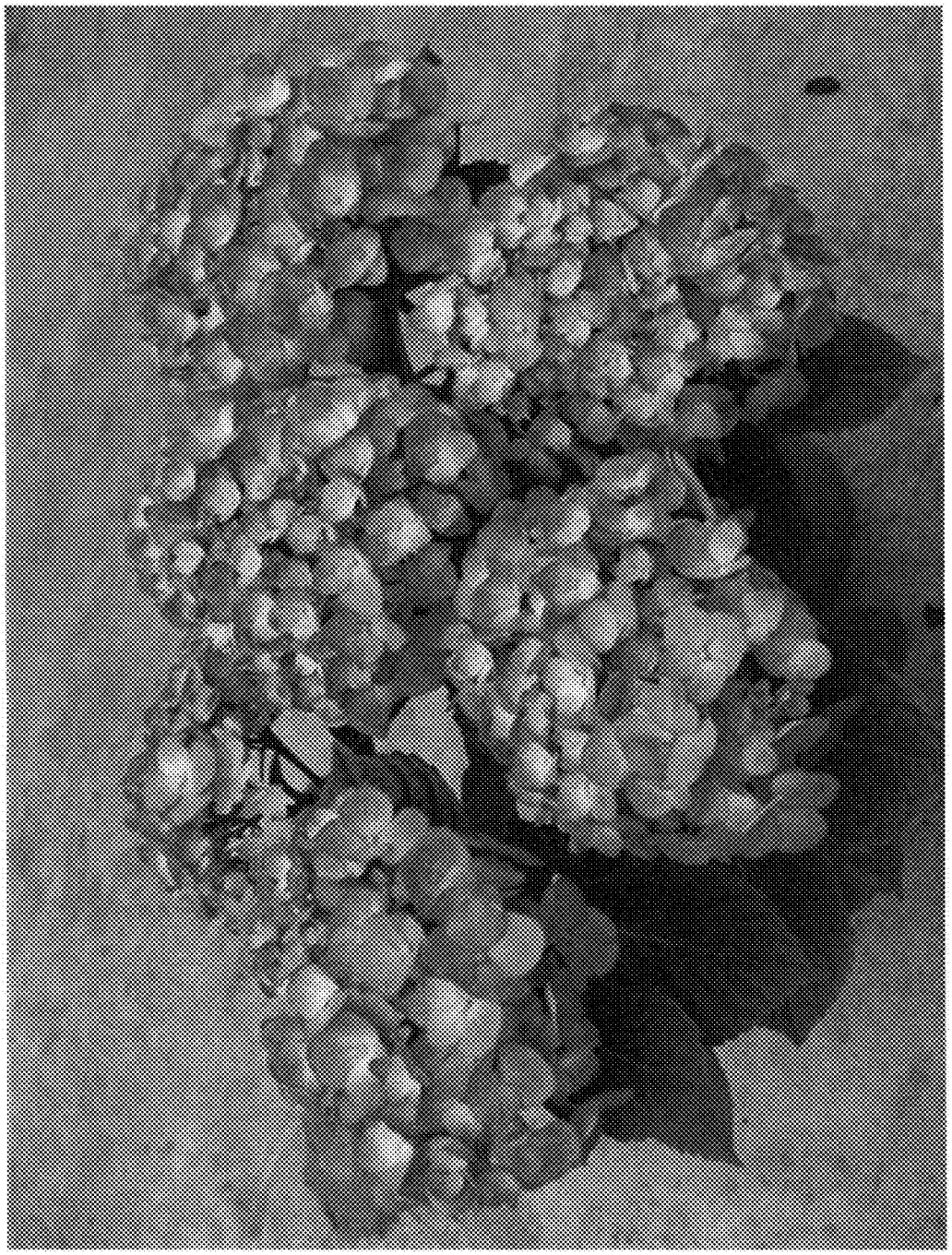
FIG. 1 is photograph of an entire plant of the new variety.
Figure 2:
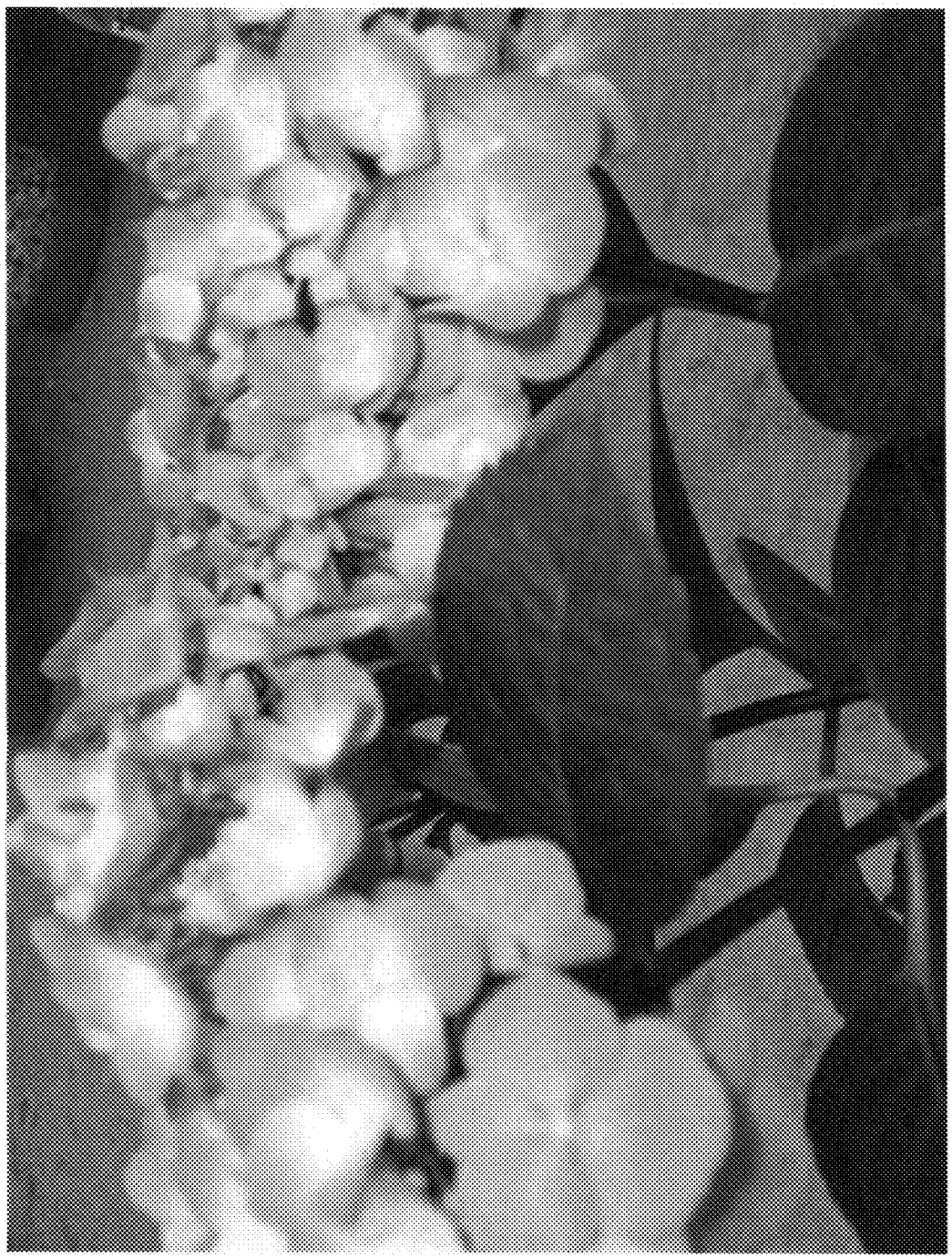
FIG. 2 is a close-up photograph of the stems of the new variety.

The following detailed description sets forth characteristics of the new cultivar. The plants were grown in 15 cm. pots, 8 per $m^2$, in ordinary potting soil with granulated fertilizers at a pH of 6.0. The plants were two years old when described. Measurements and color readings of the plants were taken in Salgen-Hausen, Germany under natural light. Color references are primarily to the HTML Color Chart.

PLANT

Time to initiate roots: About 14 days at 22° C.

Time to develop roots: About 18 days at 18-20° C.

Rooting habit: Moderate.

Time to produce a finished flowering plant from a rooted cutting: About 48 weeks in a 15 cm. container.

Form: Mounded.

Height (from media surface to top of foliage): 35.0-40.0 cm.

Height (from media surface to top of flowers): 40.0-45.0 cm.

Plant diameter: 33.0 cm.

Vigor: Good.

Strength: Good.

Branching habit: Moderately-branched.

Trunk:
*Main trunk length.*—8.0 cm.
*Diameter.*—1.0 cm.
*Color.*—00 00 00.
*Texture.*—Shiny.
*Pubescence.*—Absent.
*Internode length.*—1.5-2.0 cm.
Lateral branches:
*Length.*—Young: 35.0 cm. Mature: 8.0 cm.
*Diameter.*—Young: 0.5 cm. Mature: 0.5 cm.
*Internode length.*—5.0-6.0 cm.
*Texture.*—Shiny.
*Pubescence.*—Absent.
*Color.*—Young: Chartreuse 7F FF 00. Mature: Dark Green 00 64 00.
Foliage:
*Arrangement.*—Single.
*Stipules.*—Length: 4.0 cm. Width: 3.0 cm. Color (both surfaces): Forest Green 22 8B 22.
*Size of leaf.*—Length: 7.0 cm. Width: 4.0 cm.
*Shape of leaf* (*generally*).—Young: Aristate. Mature: Aristate.
*Shape of apex.*—Lanceolate and attenuate.
*Shape of base.*—Round.
*Texture.*—Shiny.
*Aspect.*—V-formed.
*Margin type.*—Serrate.
*Pubescence.*—None present.
*Color.*—Young leaves: Upper surface: Forest Green 22 8B 22. Lower surface: Forest Green 22 8B 22. Mature leaves: Upper surface: Dark Green 00 64 00. Lower surface: Dark Green 00 64 00.
*Petiole.*—Shape: Square. Length: 1.5 cm. Diameter: 1.5 cm. Color: Maroon 80 00 00.
*Veins.*—Color: Upper surface: EE E8 AA. Lower surface: Maroon 80 00 00.

FLOWER

Natural flowering season: May through September in Ermelo, The Netherlands.
Blooming habit: Early blooming and continuous.
Bud:
*Shape of cluster.*—Round.
*Diameter of cluster.*—10.0 cm.
*Number of buds per cluster.*—Approximately 50.
*Shape.*—Ball.
*Length.*—2.0 mm.
*Width.*—1.0 mm.
Inflorescence:
*Shape.*—Round.
*Length.*—12.0 cm.
*Diameter.*—12.0 cm.
*Average number of flowers per inflorescence.*—Approximately 40.
*Typical number of inflorescences per plant.*—5 or more, depending on frost conditions that year.
*Lastingness of an individual flower.*—6 to 8 weeks.
*Lastingness of an inflorescence.*—6 to 8 weeks.
Petals:
*Number per flower.*—4.
*Color.*—Upper surface: Maroon 80 00 00. Lower surface: Pale Violet-Red DB 70 93.
*Shape.*—Square.
*Length.*—1.5 cm.
*Width.*—1.5 cm.
*Apex.*—Lanceolate and attenuate.
*Base.*—Round.
*Margin.*—Entire.
*Texture.*—Shiny.
*Tonality from a distance.*—Full and strong colored flowers.
Sepals:
*Number per flower.*—4.
*Color.*—Upper surface: Maroon 80 00 00. Lower surface: Fire Brick B2 22 22.
*Shape.*—Lanceolate and attenuate.
*Length.*—3.0 mm.
*Width.*—1.5 mm.
*Apex.*—Lanceolate and attenuate.
*Base.*—Triangular.
*Margin.*—Entire.
*Texture.*—Shiny.
*Fused.*—No.
Petaloids:
*Quantity.*—4.
*Shape.*—Round.
*Length.*—2.0 mm.
*Width.*—1.0 mm.
*Color.*—Upper surface: White FF FA F0. Lower surface: White FF FA F0.
Pedicels:
*Length.*—1.0 cm.
*Diameter.*—1.0 mm.
*Color.*—Dark Red 8B 00 00.
Peduncles:
*Length.*—2.0 to 3.0 cm.
*Diameter.*—3.0 mm.
*Texture.*—Shiny.
*Color.*—Green 00 64 00.
Stamens:
*Number per fertile flower.*—10.
*Filament.*—Length: 3.0 to 6.0 mm. Color: White FF FA F0.
*Anthers.*—Shape: Elongated oval. Length: 2.0 to 3.0 mm. Color: White FF FA F0.
*Pollen.*—Color: Yellow FF FF 00. Amount: Abundant.
Pistils:
*Number.*—1.
*Length.*—5.0 mm.
*Style.*—Length: 5.0 mm. Color: White FF FA F0.
*Stigma.*—Number: 1. Shape: Compact. Color: Yellow FF FF 00. Size: 0.5 $cm^2$.
*Ovaries* (*superior*).—Length: 1.5 mm. Width: 1.5 mm. Color: Yellow FF FF 00.
Fragrance: None observed.
Disease resistance: Tolerant to botrytis and powdery mildew.
Temperature tolerance: Very good.
Drought tolerance: Medium.

I claim:

1. A new and distinct variety of *Hydrangea* plant substantially as shown and described herein.

* * * * *